United States Patent
Mueller

(10) Patent No.: US 6,289,234 B1
(45) Date of Patent: Sep. 11, 2001

(54) METHOD FOR TIME-RESOLVED AND LOCATION-RESOLVED PRESENTATION OF FUNCTIONAL BRAIN ACTIVITIES WITH MAGNETIC RESONANCE AND APPARATUS FOR THE IMPLEMENTATION OF THE METHOD

(75) Inventor: Edgar Mueller, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/453,284

(22) Filed: Dec. 2, 1999

(30) Foreign Application Priority Data

Dec. 2, 1998 (DE) ................................. 198 55 671

(51) Int. Cl.[7] ........................................... A61B 5/055
(52) U.S. Cl. ............................... 600/410; 324/309
(58) Field of Search ............................ 600/509, 407, 600/410, 425, 587, 544, 545, 411; 324/307, 309

(56) References Cited

U.S. PATENT DOCUMENTS

| 4,945,478 | * | 7/1990 | Merickel et al. | 364/413.22 |
| 5,603,319 | * | 2/1997 | Kuhara et al. | 128/653.2 |
| 5,603,322 | * | 2/1997 | Jesmanowicz et al. | 128/653.2 |
| 5,632,276 | * | 5/1997 | Eidelberg et al. | 128/653.1 |
| 5,662,112 | | 9/1997 | Heid . | |
| 5,732,702 | * | 3/1998 | Mueller et al. | 128/653.2 |
| 5,794,621 | * | 8/1998 | Hogan et al. | 128/653.1 |
| 6,002,254 | * | 12/1999 | Kassai et al. | 324/306 |
| 6,009,208 | * | 12/1999 | Mitra et al. | 382/254 |
| 6,018,675 | * | 1/2000 | Apkarian et al. | 600/407 |
| 6,073,041 | * | 6/2000 | Hu et al. | 600/410 |
| 6,099,319 | * | 8/2000 | Zaltman et al. | 434/236 |

\* cited by examiner

*Primary Examiner*—Marvin M. Lateef
*Assistant Examiner*—Eleni Mantis Mercader
(74) *Attorney, Agent, or Firm*—Schiff Hardin & Waite

(57) ABSTRACT

In a method for time-resolved and location-resolved presentation of functional brain activities with magnetic resonance and apparatus for the implementation of the method, the following control sequences are automatically implemented with a control unit on the basis of user inputs: generation of stimulation sequences for an examination subject, control of the data acquisition, post-processing and presentation of the data. A patient under examination can influence the control execution during the control execution.

5 Claims, 1 Drawing Sheet

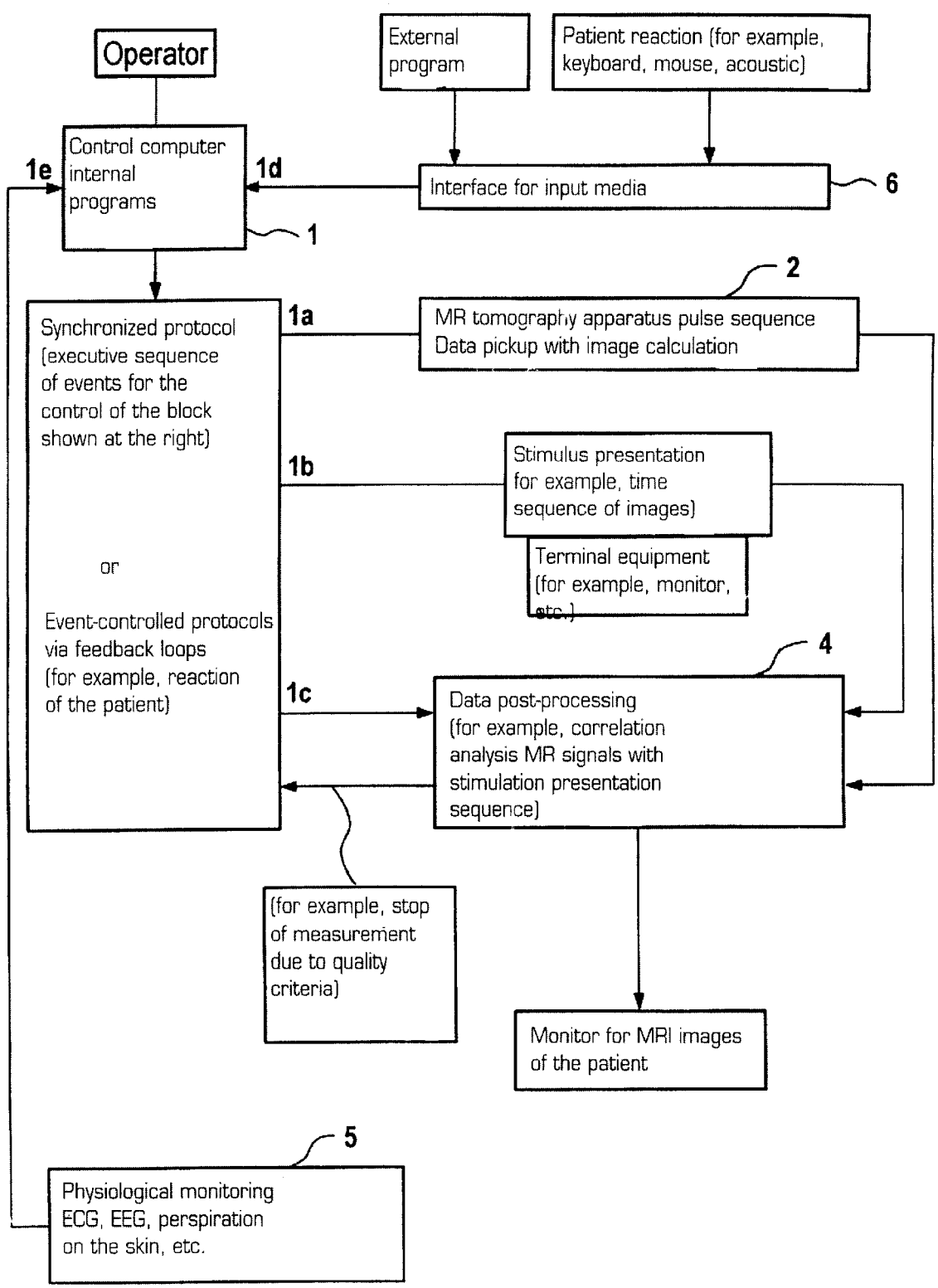

METHOD FOR TIME-RESOLVED AND LOCATION-RESOLVED PRESENTATION OF FUNCTIONAL BRAIN ACTIVITIES WITH MAGNETIC RESONANCE AND APPARATUS FOR THE IMPLEMENTATION OF THE METHOD

BACKGROUND OF THE INVENTION

1. Field of the Invention

The present invention is directed to a method for the presentation of functional brain activities in a time-resolved and location-resolved manner, by means of magnetic resonance, as well as to a magnetic resonance apparatus for implementing such a method.

2. Description of the Prior Art

U.S. Pat. No. 5,662,112 discloses a method for time-resolved and location-resolved presentation of functional brain activities. A stimulation sequence is thereby applied to the patient and image data from the brain are acquired with an MR tomography apparatus. In order to separate the signal changes caused by brain activities from other signal changes, for example caused by movements, a correlation coefficient between the stimulation function and the obtained chronological signal curve is calculated for each pixel of the acquired image data.

For example, visual, acoustic, motor or olfactory stimuli of the sensory organs can be used for stimulation of brain activities. Cognitive problems are also often applied. The data acquisition for the MR image is then synchronized with this stimulation sequence. The post-processing, i.e., for example, the aforementioned correlation, ensues by post-processing the data acquired at the MR tomography apparatus with the assistance of specific programs that, in conventional systems, are not integrated into the general control execution. The complexity of the functional imaging requires the use of experts who interactively work at parts of the overall problem. Dependent on the experimental conditions, different post-processing paths are utilized. Heretofore, thus, functional MR examinations have been extremely time-consuming and have required considerable special knowledge in addition to dexterity of a trained MR radiologist.

SUMMARY OF THE INVENTION

An object of the present invention is to provide a method for time-resolved and location-resolved presentation of functional brain activities and an apparatus for the implementation of the method wherein the presentation of the functional brain activities with MR tomography is facilitated.

The above object is achieved in accordance with the principles of the present invention in a method for time-resolved and location-resolved presentation of functional brain activities by means of magnetic resonance, employing a control unit which automatically controls executive sequences on the basis of operator inputs, these executive sequences including generating stimulation sequences for an examination subject, controlling the acquisition of data from the examination subject after stimulation, and post-processing and presentation of the acquired data, and wherein the examination subject can influence at least portions of these executive sequences during the control execution.

The above object is also achieved in accordance with the principles of the present invention in a magnetic resonance apparatus for obtaining data for a time-resolved and location-resolved presentation of functional brain activities, having a control computer with a control input for a pulse sequence for operating the magnetic resonance apparatus, a control input for a stimulation unit for stimulating an examination subject, and a control input for processing data acquired from the examination subject dependent on a stimulus produced by the stimulation unit, and wherein the control computer also has an input for entering physical parameters of the examination subject. The control computer can also include input for an input unit which can be actuated by the examination subject during the data acquisition process.

By utilizing a specific control unit wherein all steps required for the functional imaging are integrated, an automatic execution of specific programs for the functional MR imaging is possible. Such programs, as is generally standard in MR imaging, can be called as protocols, so that the measuring execution itself can be implemented in a repeatable fashion by medical assistants. The use of special technical personnel trained for functional imaging is eliminated for the measuring execution. Of course, special knowledge is required for the interpretation of the images obtained.

DESCRIPTION OF THE DRAWING

The single FIGURE is a flowchart for a data acquisition procedure in accordance with the inventive method, and implementable in the inventive magnetic resonance apparatus.

DESCRIPTION OF THE PREFERRED EMBODIMENTS

An exemplary embodiment of the invention is explained in detail with reference to the figure. This figure represents a flowchart for the measuring procedure. The control computer 1 controls the overall executive sequence of the functional imaging. The control computer shown separately here can, of course, be a component of the overall system control, whereby the system control then merely requires additional software modules and interfaces for inputs. There are fundamentally two possibilities for the measuring execution described in the form of a protocol:

the measuring sequence can ensue according to a predetermined protocol, or the measuring sequence can ensue according to an event-controlled protocol via a feedback loop, for example on the basis of a reaction on the part of the patient.

In any case, a sequence protocol is handed over to the other components of the system. These are the actual MR tomography apparatus 2, the stimulus presentation 3 and the data post-processing 4. The stimulus presentation, as indicated above, can be of many types. For example, it can be a time sequence of images. To this end, a terminal equipment is generally required that outputs corresponding signals. In the case of a visual stimulation with images this, for example, could be a monitor at which the patient looks. Simultaneously with the presentation and possibly synchronized therewith, a registration of measured signals with subsequent image calculation ensues in the MR tomography apparatus according to block 2.

Likewise controlled by the protocol specified in greater detail above, a data post-processing ensues according to block 4. As disclosed in the aforementioned U.S. Pat. No. 5,662,112, a correlation analysis of the stimulation function with the acquired image information can ensue in order to extract functional information from the image information. This information is then displayed on a monitor.

The control computer can be operated by an operator. As already stated, the job of the operator is substantially easier due to the automation. In the simplest case, the operator merely has to start the measuring sequence as soon as the patient is ready for the examination. Typically, a number of examination runs in the form of MR protocols that have proven to be of particular diagnostic usefulness from clinical experience are made available. The operator then merely has to select between the examination sequences available. Physiological parameters of the patient can also influence the control computer. For example, the measurement sequence can be made dependent on the ECG or EEG of the patient, on the development of perspiration on the patient's skin, etc. These parameters can influence the stimulus presentation and also can influence the pulse frequency applied for the data registration. An active patient reaction can be taken into consideration via an interface 6 for input media 6, for example via a keyboard, a mouse or an acoustic input. During the measuring sequence, for example the execution of the stimulation sequences, the patient can thereby influence the data acquisition and the presentation of the functional images. An external program can also influence the measuring sequence via this interface 6.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for obtaining magnetic resonance data representing functional brain activities of an examination subject, said apparatus comprising:

a magnetic resonance data acquisition system;

a stimulation unit for stimulating an examination subject in said magnetic resonance data acquisition system; and a control unit connected to said magnetic resonance data acquisition system and to said stimulation unit for operating said stimulation unit and said magnetic resonance data acquisition system by the executing executive sequences, said control unit having first control output for causing said stimulation unit to emit a stimulus perceivable by said examination subject, a second control output for supplying a pulse sequence to said magnetic resonance data acquisition system for operating said magnetic resonance data acquisition system to obtain magnetic resonance data from said examination subject after said stimulus, a third control output for emitting said magnetic resonance data, and an input interacting with said examination subject to obtain physical parameters from said examination subject during execution of said executive sequences and entering said physical parameters of said examination subject into said control unit for influencing at least one of said pulse sequence and said stimulus during execution of said executive sequences; and display and processing means connected to said third control output for processing said magnetic resonance data to generate a time-resolved and location-resolved presentation of functional brain activities of said examination subject.

2. An apparatus as claimed in claim 1 further comprising an input interface operable by said examination subject, and wherein said control unit comprises a further input, connected to said input interface, to allow said examination subject to make an entry into said control unit during acquisition of said magnetic resonance data for influencing at least one of said pulse sequence and said stimulus.

3. A method for time-resolved and location-resolved presentation of functional brain activities using magnetic resonance, comprising the steps of:

executing a plurality of executive sequences in a control unit dependent on operator inputs to said control unit, said executive sequences including generating stimulation sequences for stimulating an examination subject, controlling acquisition of magnetic resonance data from said examination subject after stimulation, and post-processing and presenting said magnetic resonance data; and allowing said examination subject to make an entry into said control unit during at least a portion of said executive sequences for influencing at least a portion of said executive sequences.

4. A method as claimed in claim 3 comprising operating said control unit with a plurality of selectable, preprogrammed sets of said executive sequences.

5. A method as claimed in claim 3 comprising entering physiological parameters of said examination subject into said control unit to influence said executive sequences.

* * * * *